(12) United States Patent
Rho

(10) Patent No.: US 6,428,485 B1
(45) Date of Patent: Aug. 6, 2002

(54) METHOD FOR TESTING HEARING ABILITY BY USING INTERNET AND RECORDING MEDIUM ON WHICH THE METHOD THEREFOR IS RECORDED

(75) Inventor: YunSung Rho, 502-804 Samhwan Apt. Inchang-dong Kuri-shi, Kyunggido (KR)

(73) Assignees: Gye-Won Sim; San-Don Sim, both of Seoul; YunSung Rho, Kyunggido, all of (KR)

( * ) Notice: Subject to any disclaimer, the term of this patent is extended or adjusted under 35 U.S.C. 154(b) by 0 days.

(21) Appl. No.: 09/537,613

(22) Filed: Mar. 29, 2000

(30) Foreign Application Priority Data

Jul. 2, 1999 (KR) ............................................ 99-26584

(51) Int. Cl.[7] .............................................. A61B 5/00
(52) U.S. Cl. ...................................................... 600/559
(58) Field of Search ................................. 600/559, 300; 73/585; 381/1–369

(56) References Cited

U.S. PATENT DOCUMENTS

| | | |
|---|---|---|
| 3,169,171 A | 2/1965 | Wachs et al. |
| 3,808,354 A | 4/1974 | Feezor et al. |
| 3,809,811 A | 5/1974 | Delisle et al. |
| 4,964,161 A | 10/1990 | Trowbridge, Jr. |
| 5,012,513 A | 4/1991 | Dale et al. |
| 5,119,826 A | 6/1992 | Baart de la Faille |
| 5,601,091 A * | 2/1997 | Dolphin .................... 600/559 |
| 5,928,160 A * | 7/1999 | Clark et al. ................ 600/559 |
| 6,086,541 A | 7/2000 | Rho |

* cited by examiner

*Primary Examiner*—Kevin Shaver
*Assistant Examiner*—Pamela L Wingood
(74) *Attorney, Agent, or Firm*—Merchant & Gould P.C.

(57) ABSTRACT

A method for testing hearing ability by which a patient can test his hearing ability any time and any place without spending time on visiting the hospital and making reservation and preparing expensive equipments for a self-test, is provided. When the method for testing the hearing ability is selected by a tested person connected by the Internet, sounds having different volumes of a predetermined frequency bandwidth are sequentially reproduced according to the selected hearing ability testing method. The average threshold value and the hearing hardness grade of the tested person are calculated and displayed according to the response of the tested person for the reproduced sounds. A hearing ability test is divided into a test in a low band, a test in a conversation band, and a test in a high band, respectively. The hearing ability test in the conversation band is divided into a continuous test and a test performed, while looking at a screen. In the respective tests, sounds having different frequencies and volumes are reproduced in a predetermined order. The threshold value and the hearing hardness grade of the tested person in each band is calculated and displayed according to the responses of the tested person. When the hearing hardness grade of the tested person is displayed, symptom of diseases and measures for the diseases according to the hearing hardness grade are also displayed. Therefore, the tested person can maintain his hearing ability.

12 Claims, 3 Drawing Sheets

METHOD FOR TESTING HEARING ABILITY BY USING INTERNET AND RECORDING MEDIUM ON WHICH THE METHOD THEREFOR IS RECORDED

BACKGROUND OF THE INVENTION

1. Field of the Invention

The present invention relates to a method for testing hearing ability, and more particularly to a method for testing hearing ability by using an Internet site.

2. Description of the Related Art

The program according to the present invention, which is mentioned hereinafter, is a computer program for connecting a user's browser such as Internet explorer and Netscape which is connected to the Internet to an Internet server by means of a hyper text markup language (HTML) and a common gateway interface (CGI), which can realize texts, images, sound, and moving pictures in an Internet communication network, i.e., a world wide web (WWW).

Ears which are important sense organs that a man has contribute to information gathering. However, hearing ability gradually declines as a man grows old. Accordingly, it is much likely that a patient does not recognize the attenuation of his hearing ability unless his hearing ability rapidly attenuates. Also, even though the patient recognizes the attenuation of his hearing ability, the attenuation of the hearing ability is not immediately treated or corrected in many cases since his busy daily lives prevent him from visiting the hospital.

In particular, noise in working spaces has recently increased due to industrial developments and rapid changes in industrial environments and the hardness of hearing caused by these has also increased. Accordingly, devices for blocking noise and noise free working environments are required for workers. In general, when a man works in a noisy working area for a long time, a human body becomes accustomed to noise. In other words, the noise is heard loud at first and them, weak as time passes. Therefore, the damage of the auditory nerve is accelerated and a worker does not recognize a change in his hearing ability.

Such a change in hearing ability is referred to as hardness of hearing which is divided into rapid hardness of hearing where the hearing ability rapidly attenuates and slow hardness of hearing where the hearing ability slowly attenuates. The slow hardness of hearing is difficult to be recognized. Since the rapid hardness of hearing can be easily cured when it is diagnosed at early stage, it is very important to recognize the rapid hardness of hearing at an early stage.

In order to recognize the slow hardness of hearing and to cure it at an early stage, the patient should periodically visit the hospital and test his hearing ability by means a screening teat. Otherwise, for a self-test, it is necessary to prepare a tuning fork that can generate very pure sound and to periodically test the hearing ability.

However, such hearing diagnosis method has the following disadvantages: in case that it is necessary to visit the hospital, inconveniences such as time loss, a need for reservation to see a doctor, etc., may occur. Also, in the case of the self-test, the patient must prepare expensive test equipments.

A method for solving the above problems is disclosed in the U.S. patent application Ser. No. 09/285351 now U.S. Pat. No. 6,086,541 filed by the assignee of the application on Apr. 2, 1999 and allowed on Jan. 31, 2000 under the title a method for testing hearing ability by using automatic voice response system (ARS) executed by a computer, a program therefor, and a noise blocker.

In the hearing ability testing method disclosed in the U.S. patent application Ser. No. 09/285351, now U.S. Pat. No. 6,086,541 when a tested person makes a phone call, the ARS and a hearing ability testing program are executed by a computer and the hearing ability of the tested person is tested. The hearing ability of the tested person is sequentially tested in a predetermined hearing ability testing order according to predetermined hearing ability grades. The computer explains the hearing ability grade of the tested person, symptoms accompanied by the corresponding hearing ability of the tested person and necessary measures and cautions based on the hearing ability of the tested person, by executing the programs. According to the hearing ability testing method, the hearing ability of the tested person is easily tested and the symptoms accompanied by the corresponding hearing ability of the tested person and the measures and cautions based on the hearing ability of the tested person are notified. Accordingly, it is possible to cure the hardness of hearing at an early stage.

However, only a telephone is used for the above method and it is difficult for the tested person remember all the symptoms and measures which were mentioned in the ARS. Also, it is difficult to correctly test the hearing ability when the quality of sound of the telephone is not good. Also, the tested person must pay for expensive telephone charges in order to use the ARS.

SUMMARY OF THE INVENTION

In order to solve the above problems, it is an object of the present invention to provide a method for a tested person testing his hearing ability and notifying the tested person symptoms accompanied by the hearing ability grade of the tested person and measures for the symptoms, without spending time on visiting the hospital and making the reservation and preparing expensive testing equipments.

It is another object of the present invention to provide a recording medium on which the above testing method is recorded.

To achieve the first object, there is provided a method for testing hearing ability using the Internet, including the steps of: a tested person selecting a method for testing the hearing ability by connecting to an Internet home page: reproducing sound having a predetermined volume of a predetermined frequency bandwidth for a set time; and calculating the hearing hardness grade of the tested person according to whether the tested person responds to the reproduced sound.

According to the feature of the present invention, the set time is one second, the sound includes a low band of frequencies 250 Hz and 500 Hz, a conversation band of frequencies 1,000 Hz and 2,000 Hz, and a high band of frequencies 4,000 Hz and 8,000 Hz and has the volume between 0 dB and 80 dB in each frequency.

The average threshold value of the tested person is calculated according to the response of the tested person and the hearing hardness grade of the tested person is displayed as a normal state, light hearing hardness, medium hearing hardness, medium-high hearing hardness, high hearing hardness, high frequency hearing loss, or low frequency hearing loss.

To achieve the second object, there is provided a recording medium for the method Internet based hearing ability testing. A magnetic disk, an optical disk, and a hard disk can be used as the recording medium.

The method for testing the hearing ability according to the present invention is performed by the Internet network.

When the tested person visits a hearing ability test site, inputs his personal information according to the method for testing the hearing ability of the present invention, and selects the test method, the hearing ability is tested by a common gateway interface (CGI) program. The sounds having different frequencies and volumes are sequentially reproduced according to the hearing ability testing method selected by the tested person. The tested person checks whether the reproduced sounds are heard.

The hearing ability grade of the tested person is calculated and displayed according to the response of the tested person and symptoms of diseases and measures for the diseases according to the hearing ability of the tested person are displayed in the CGI program. Therefore, the tested person can test his hearing ability any time any place without spending time on visiting the hospital and making the reservation and preparing expensive equipments for a self-test.

BRIEF DESCRIPTION OF THE DRAWING(S)

The above objects and advantages of the present invention will become more apparent by describing in detail a preferred embodiment thereof with reference to the attached drawings in which.

DESCRIPTION OF THE PREFERRED EMBODIMENT

Figure 1:
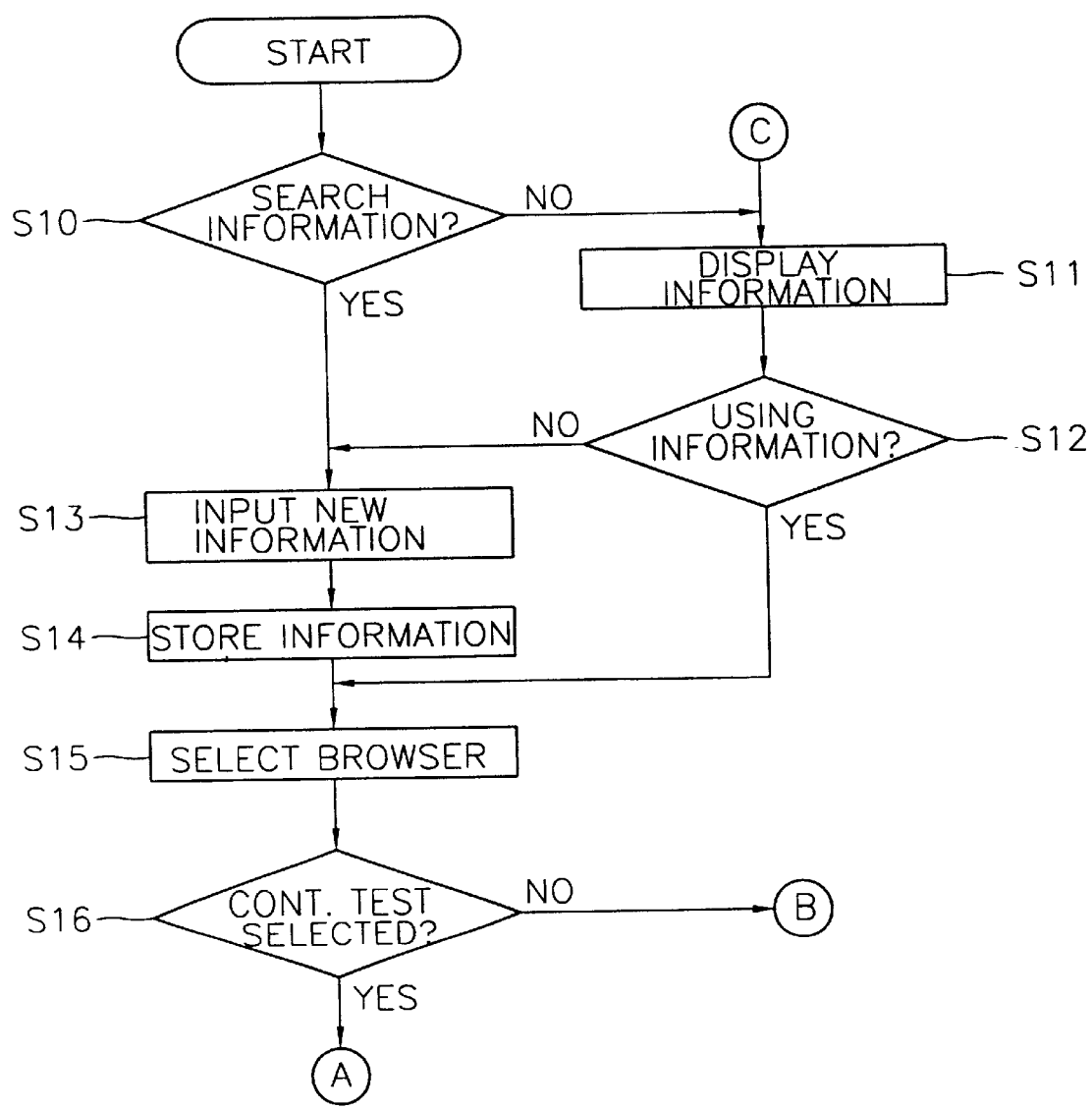
FIG. 1 is a flowchart for showing the steps of inputting personal information on a tested person and selecting a method for testing the hearing ability of the tested person.
Figure 2:
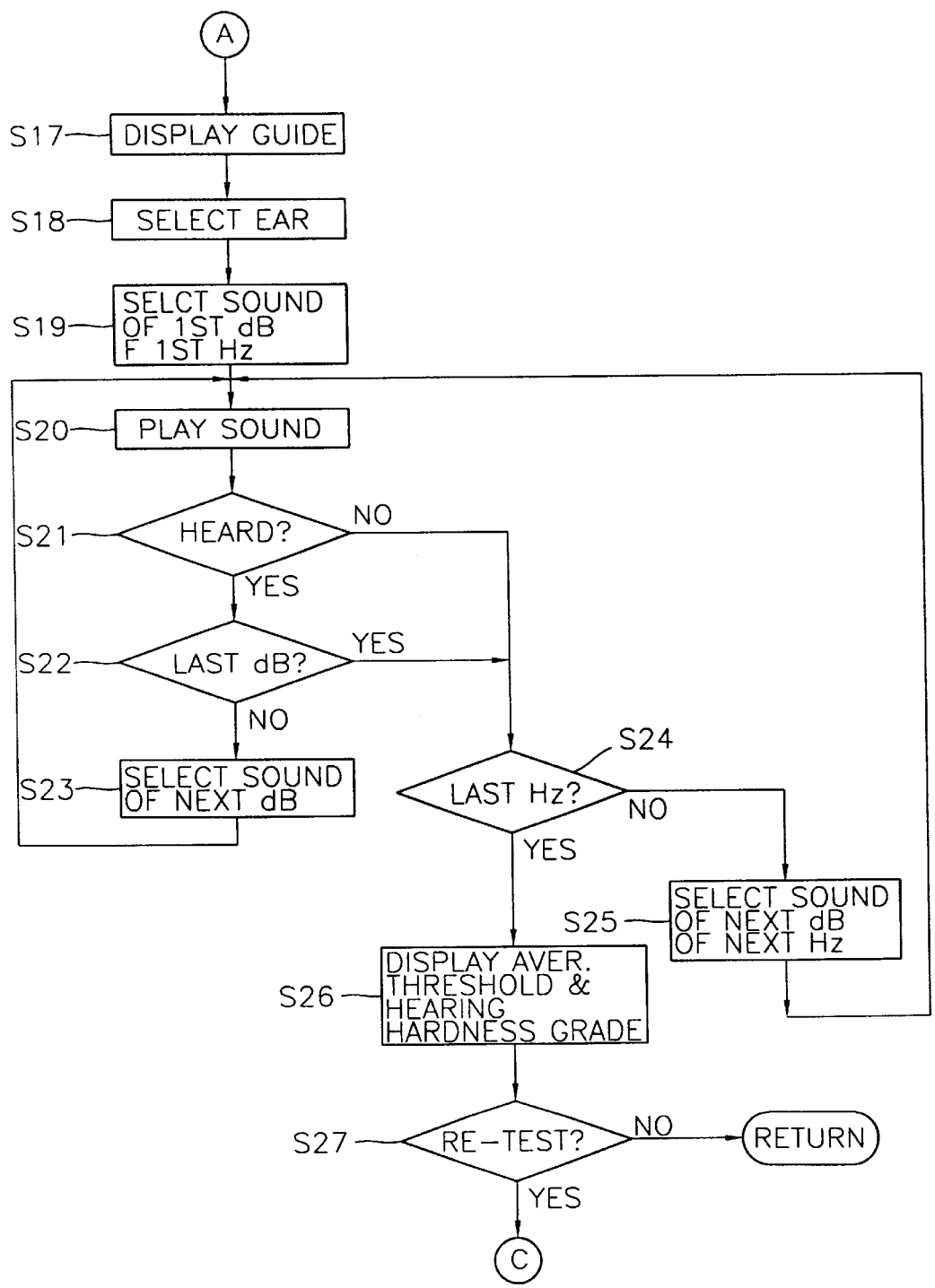
FIG. 2 is a flowchart for showing steps of continuously testing the hearing ability in a conversation band, in a method for testing the hearing ability according to the present invention.
Figure 3:
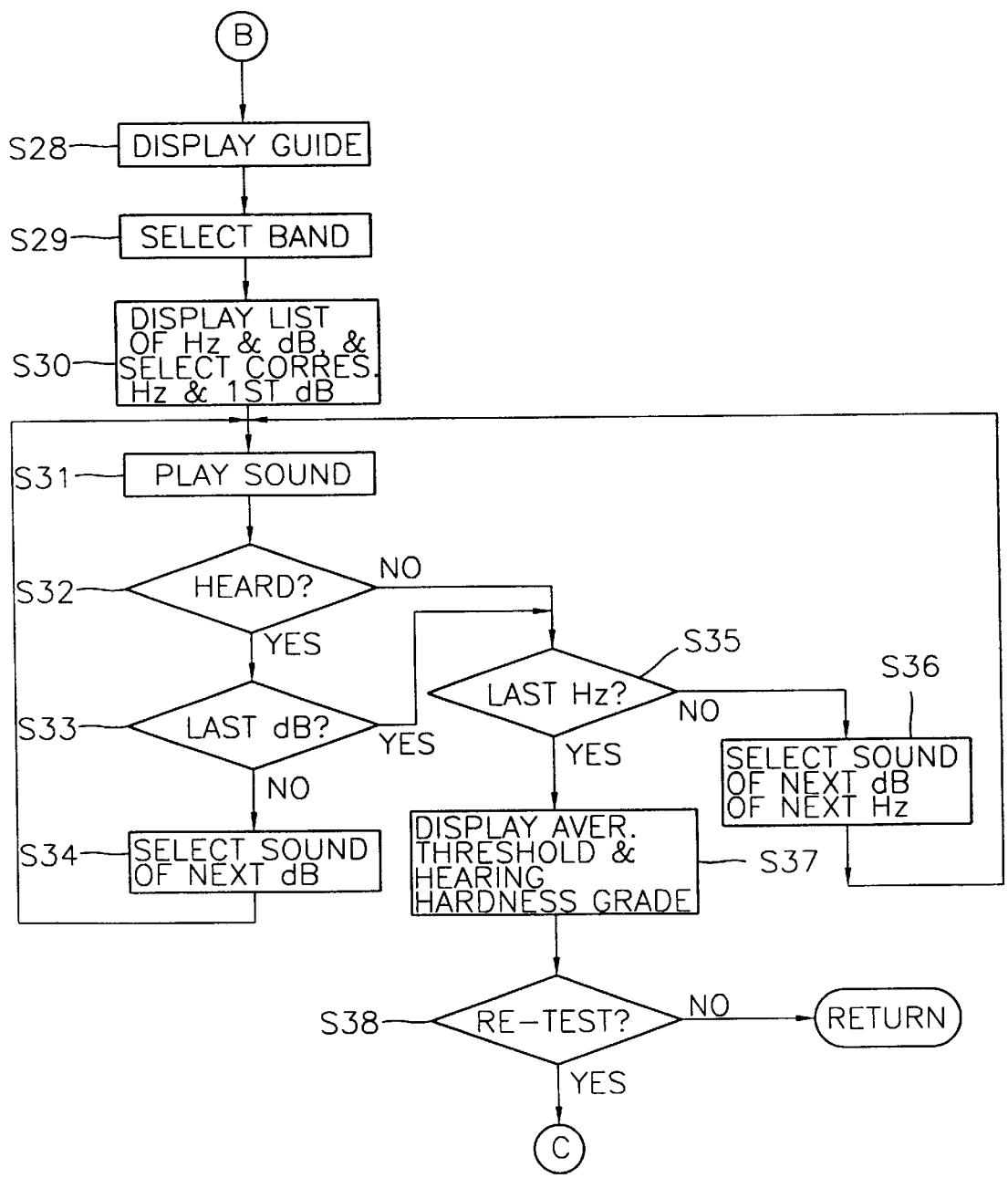
FIG. 3 is a flowchart for showing steps of testing the hearing ability, while looking at a screen, in the method for testing the hearing ability according to the present invention.

FIGS. 1 through 3 are flowcharts for describing a method for testing hearing ability according to a preferred embodiment of the present invention. FIG. 1 is a flowchart for showing the steps of inputting personal information on a tested person and selecting a method for testing the hearing ability of the tested person. FIG. 2 is a flowchart for showing steps of continuously testing the hearing ability in a conversation band, in a method for testing the hearing ability according to the present invention. FIG. 3 is a flowchart for showing steps of testing the hearing ability, while looking at a screen, in the method for testing the hearing ability according to the present invention.

The method for testing the hearing ability according to the preferred embodiment of the present invention, where the hearing ability is tested on an Internet network, includes the steps of checking and inputting personal information on a tested person, selecting a method for testing the hearing ability (Step S16), and performing the selected method for testing the hearing ability. The tested person can test his hearing ability by connecting to the Internet through an Internet connection program and a MODEM and opening a home page which provides a test on the hearing ability. Internet through an Internet connection program and a MODEM and opening a home page which provides a test on the hearing ability.

The step of inputting the personal information includes the steps of checking the information on the tested person (Step S10), searching the information on the tested person according to the selection of the tested person and displaying the searched information (Step S11), selecting whether to continuously use the displayed information on the tested person (Step S12), inputting the personal information on the tested person (Step S13), storing the information on the tested person (Step S14), and controlling the computer of the tested person and selecting a browser (Step S15), as shown in FIG. 1.

In the step of checking the information on the tested person (Step S10), a message for asking the tested person whether to search the information on the tested person is displayed on a screen. The personal information on the tested person is stored in a memory device of a server for providing a hearing ability test, for example, a hard disk. The information on the tested person stored in the memory device of the server is searched and displayed on the screen in the step of displaying the information (Step S11). The tested person checks the personal information on the tested person displayed on the screen and selects whether to continuously use the information in the step of selecting whether to continuously use the information (Step S12). The tested person inputs his personal information in the step of inputting the personal information (Step S13). The input personal information on the tested person is stored in the memory device of the server in the step S14. A button for selecting a browser used by the tested person, for example, MS-Explorer and Netscape is displayed on a screen together with the message in the step of selecting the browser (Step S15). The step of inputting the information including the above steps is programmed by a hyper text markup language (HTML).

A message for letting the tested person select either a method for continuously testing the hearing ability or a method for testing the hearing ability, while looking at the screen is displayed on the screen and one of the method for testing the hearing ability is selected by the tested person in the step of selecting the method for testing the hearing ability (Step S16).

FIG. 2 shows the continuous steps of testing the hearing ability (Steps S17 through S28), which are the step of displaying a guide for explaining the method for testing the hearing ability on the screen (Step S17), the step of the tested person reading the guide and selecting a ear whose hearing ability is to be tested (Step S18), the step of selecting sound having a predetermined frequency and a predetermined dB in the conversation band (Step S19), the step of reproducing the selected sound (Step S20), the step of checking whether the reproduced sound is heard (Step S21), the step of checking whether the reproduced sound is the sound having the last dB of the corresponding frequency when the reproduced sound is heard (Step S22), the step of selecting the sound having the dB reduced by a set dB from the dB of the reproduced sound (Step S23), the step of checking whether the reproduced sound is the sound having the last frequency in the conversation band when the reproduced sound is not heard or the reproduced sound is the sound having the last dB of the corresponding frequency (Step S24), the steps of selecting the sound having the next frequency when the reproduced sound is not the sound having the last frequency (Step S25), the step of calculating an average threshold value and displaying a hearing hardness grade when the reproduced sound is the sound having the last frequency (Step S27), and the step of selecting whether to perform a re-test (Step S28).

A content that a correct result can be obtained when the hearing ability is tested in a quiet place is displayed and a button is displayed so that the tested person can select the ear whose hearing ability is to be tested in the step of displaying the guide (Step 517). When the ear whose hearing ability is to be tested is selected by the tested person, the sound in the conversation band is selected by a common gateway interface (CGI) program (Step S19). The sound in the conversation band has frequencies of 500 Hz, 1,000 Hz, and 2,000 Hz. The sounds having each frequency are set to be between 0 dB and 80 dB and are reproduced in a state of being divided into 17 in units of 5 dB (Step S20). The sound is reproduced for a set time, for example, for a second.

In the step of checking whether the sound is heard (Step S21), when the tested person presses an enter button displayed on the screen within a predetermined time, for example, 5 seconds, it is determined by the CGI program that the tested person heard the reproduced sound. In the step of checking the sound having the last dB (Step S22), it is determined whether the reproduced sound is the sound having the last dB of the corresponding frequency, for example, the sound having 0 dB and 1,000 Hz when it is determined that the reproduced sound is heard. When the reproduced sound is not the sound having the last dB, the sound having the next dB reduced by the set dB from the dB of the reproduced sound is selected (Step S23) and is reproduced (Step S20).

When the reproduced sound is determined not to be heard in the step of checking whether the sound is heard (Step S21) or the reproduced sound is determined to be the sound having the last dB in the step of checking the sound having the last dB (Step S22), it is determined whether the reproduced sound is the sound having the last frequency in the conversation band (Step S24). When the reproduced sound is not the sound having the last frequency, the sound having 80 dB of the next frequency is selected (Step S25). When the reproduced sound is the sound having the last frequency, the average threshold value of the tested person is calculated and the hearing hardness grade is displayed on the screen (Step S26). The sounds having the respective frequencies are reproduced in the order of the sounds having frequencies 1,000 Hz, 2,000 Hz, 1,000 Hz, and 500 Hz. In each frequency, the sounds are reproduced in the order of the sounds having volumes 80 dB, 75 dB, 10 dB, 5 dB, and 0 dB. The threshold value with respect to the sound 1,000 Hz is excluded. The average threshold value of 2,000 Hz, 1,000 Hz, and 500 Hz is calculated. Then, the hearing hardness grade according to the average threshold value, symptoms accompanied by the hearing hardness, and measures based on the hearing ability are displayed.

When the re-test is selected by the tested person in the step of selecting the re-test (Step S27), the steps of displaying the information (Step S11) is performed again. When the re-test is not selected, the process returns.

FIG. 3 is a flowchart for showing steps of testing the hearing ability, while looking at a screen, in the method for testing the hearing ability according to the present invention. As shown in FIG. 3, the method for testing the hearing ability, while looking at the screen includes the steps of displaying the guide (Step S28), selecting a band for testing the hearing ability (Step S29), displaying sounds corresponding to all the bands which can be selected in the step of selecting the band (Step S29) and selecting and displaying a sound having a predetermined frequency and a predetermined dB in the selected band for testing the hearing ability (Step S30), reproducing the selected sound (Step S31), checking whether the reproduced sound is heard (Step S32), checking whether the reproduced sound is the sound having the last dB of the corresponding frequency when the reproduced sound is heard (Step S33), selecting the sound having the dB reduced by the set dB from the dB of the reproduced sound (Step S34), checking whether the reproduced sound is the sound having the last frequency when the reproduced sound is not heard or the reproduced sound is the sound having the last db of the corresponding frequency (Step S35), selecting the frequency of the next frequency of the corresponding band when the reproduced sound is not the sound having the last frequency in the corresponding band (Step S36), calculating the average threshold value with respect to the corresponding band and displaying the hearing hardness grade when the reproduced sound is the sound having the last frequency in the corresponding band (Step S37), and selecting whether to perform the re-test (Step S38).

In the step of displaying the guide (Step S28), the content that a correct result can be obtained when the hearing ability is tested in a quiet place is displayed. In the step of selecting the band (Step S29), the tested person checks tests on the hearing ability in the conversation band, a high band, and a low band and selects one of them. In the step of displaying and selecting the sound (Step S30), the sounds having all the frequencies and all the dBs corresponding to the three hearing ability test bands are displayed by the CGI program in the form of a table and the sound in the selected band is selected. The selected sound is highlighted in the table. The sound in the conversation band is the same as the sound in the step of continuously testing the hearing ability. The sound used for the hearing ability test in the high band has the frequencies of 4,000 Hz and 8,000 Hz and is divided into 17 in units of the set dB, that is, 5 dB between 0 dB and 80 dB. Also, the sound used for the hearing ability test in the high band has the frequencies of 250 Hz and 500 Hz and is divided into 17 in units of 5 dB. The sound is heard to the tested person for the set time (Step S31).

In the step of testing the hearing ability, while looking at the screen, in the hearing ability test in the conversation band, the sound having the same frequency as the sound used for the continuous hearing ability test is reproduced in the same order as the order in which the sound is reproduced in the continuous hearing ability test. In the hearing ability test in the high band, the sounds are reproduced in the order of the sounds having frequencies 4,000 Hz and 8,000 Hz. In the hearing ability test in the low band, the sound is reproduced in the order of 250 Hz and 500 Hz. Since the steps of checking whether the sound is heard (Step S32), checking the sound having the last dB (Step S33), selecting the next sound (Step S34), checking the last frequency (Step S35), selecting the sound of the next frequency (Step S36), displaying the average threshold value and the hearing hardness grade (Step S37), and the step of selecting the re-test (Step S38) are the same as the steps of continuously testing the hearing ability (Steps S20 through S27) excluding the order of the reproduced sounds and the corresponding frequencies, description on the steps S32 through S38 will be omitted.

The method for testing the hearing ability according to the embodiment of the present invention is programmed using Visual C++ to be executed under the Windows of the Microsoft, Inc. The edition of sound is performed using Cool edit pro. The method for testing the hearing ability according to the present invention, which includes the above steps is recorded on a recording medium such as a magnetic disk, an optical disk, and a hard disk and is executed in the Internet server.

The sound means pure sound which has a pure and inherent waveform in which other waveforms which function as noises thereto are not added. The sounds having frequencies 1,000 Hz and 30 dB are stored using a voice recognition apparatus from a hearing ability test apparatus. The stored sound is compressed and amplified. The compressed and amplified sound is stored in the memory device of the server in an encoded unique file in the form of specific voice data. The term, threshold is a minimum sound intensity (volume) in which transmitted sound can be recognized by stimulating the eardrum.

The operation of the present invention will be described with reference to FIGS. 1 through 3.

First, the tested person can test his hearing ability by connecting to the Internet using the Internet connection program and the MODEM and then, a home page for providing the hearing ability test.

In the home page, when the tested person clicks a start button for executing the hearing test, a guide with respect to computer setting for the hearing ability test is displayed on the screen. The tested person controls the volume and balance of a sound card according to the guide. The content that a correct result can be obtained when the hearing ability is tested in a quiet place is included in the guide.

When the setting of the test on the hearing ability of the tested person is completed according to the guide, the tested person clicks the start button. When the tested person clicks the start button, the personal information on the tested person is tested (Step S10). When there is data on the tested person, the personal information on the tested person is displayed (Step S11) and it is asked to the tested person whether to use the displayed personal information (Step S12).

When the data on the tested person is not searched or the tested person does not continuously use the displayed data, the personal information on the tested person for testing his hearing ability is input (Step S13) and the input information is stored in the memory device of the server (Step S14).

When the displayed data on the tested person is selected to be continuously used or the data on the tested person is stored, the tested person selects the kind of the browser to be used for the hearing ability test (Step S15) and selects either the method for continuously testing the hearing ability or the method for testing the hearing ability, while looking at the screen (Step S16).

At this time, when the tested person selects the method for continuously testing the hearing ability, the hearing ability test in the conversation band is performed.

A guide for guiding the method for testing the hearing ability is displayed on an initial screen of the continuous hearing ability test (Step S17). The tested person selects the ear whose hearing ability is to be tested (Step S18). Accordingly, the hearing ability test program loads the pure sound having 1,000 Hz and 80 dB from the memory device of the server (Steps S19 and reproduces the loaded sound for a set time (a second) (Step S20).

After the sound is reproduced, the response of the tested person is awaited for a predetermined time (5 seconds). When it is determined that the tested person heard the sound (Step S21), it is determined whether the reproduced sound is the sound having the last dB of the corresponding frequency (Step S22). If the reproduced sound is not the sound having the last dB of the corresponding frequency, the next sound whose dB is reduced by 5 dB from the dB of the reproduced sound is selected (Step S23). When it is determined that the tested person did not hear the sound, namely, when the tested person does not click the enter button within the predetermined time (Step S21), it is determined whether the reproduced sound is the sound having the last frequency, that is, 500 Hz (Step S24). When the reproduced sound is not the sound having the last frequency, the sound having 80 dB of the next frequency is selected (Step S25). When the reproduced sound is the sound having the last frequency, the average threshold value of the tested person is calculated and displayed on the screen together with the hearing hardness grade (Step S22).

The reproduction of the sound and the response of the tested person are repeated until the sounds having four frequencies (1,000 Hz, 2,000 Hz, 1,000 Hz, and 500 Hz) are sequentially reproduced. In the case where the tested person does not respond within 5 seconds when the reproduced sound is the last frequency or the reproduced sound has the last frequency and 0 dB, the average threshold value of the tested person is calculated (the hearing ability threshold value with respect to initial frequency 1,000 Hz is excluded) and displayed on the screen together with the hearing hardness grade (Step S26). The hearing hardness grades consist of a normal state, light hearing hardness, medium hearing hardness, medium-high hearing hardness, and high hearing hardness. The causes of the diseases, the symptoms, and measures according to the hearing hardness grades are displayed. Therefore, the tested person can prevent ear diseases since he can be notified his hearing ability and the measures based on high hearing ability.

When the hearing ability of the selected ear of the tested person is tested, a message for asking whether to perform the re-test is displayed on the screen and the tested person selects whether to perform the re-test (Step S27). When the re-test is selected by the tested person, the personal information on the tested person is displayed again (Step S11) and the tested person can test the hearing ability of the other ear according to the above mentioned steps. When the re-test is not selected, the home page is displayed.

When the method for testing the hearing ability, while looking at the screen, is selected in the step of selecting the method for testing the hearing ability (Step S16), a guide with respect to the method for testing the hearing ability, while looking at the screen, is displayed on the screen (Step S28). The tested person selects one among the hearing ability test in the high band in which the frequencies are 4,000 Hz and 8,000 Hz, the hearing ability test in the low band in which the frequencies are 250 Hz and 500 Hz, and the hearing ability test in the conversation band in which the frequencies are 500 Hz, 1,000 Hz, and 2,000 Hz (Step S29).

When the band in which the hearing ability is to be tested is selected by the tested person, a list of all the frequencies corresponding to the low band, the high band, and the conversation band and the sounds arranged from the loud sound (80 dB) to the weak sound (0 dB) at intervals of 5 dB in each frequency bandwidth and the frequency and dB of the currently reproduced sound is highlighted (Step S30). The steps of reproducing the sound (Step S31), the tested person responding whether the sound is heard (Step S32), determining whether the reproduced sound has the last dB (Step S33), selecting the sound having the next volume (Step S34), determining whether the reproduced sound has the last frequency (Step S35), selecting the sound having the next frequency (Step S36) or calculating the average threshold value and displaying the hearing hardness grade (Step S37), and selecting the re-test (Step S38) are the same as the steps of the method for continuously testing the hearing ability excluding that the frequencies in the high band are 4,000 Hz and 8,000 Hz and the frequencies in the low band are 250 Hz and 500 Hz. Therefore, description on the steps (S31 through S38) will be omitted.

The frequencies, the volumes of the sounds, and the hearing hardness grades used for the present invention are shown in Tables 1, 2, and 3.

TABLE 1

Conversation band (the method for continuously testing the hearing ability/the method for testing the hearing ability, while looking at the screen): 500 Hz, 1,000 Hz, and 2,000 Hz

| Average threshold value | Hearing hardness grade |
| --- | --- |
| 0dB through 25dB | Hearing ability of the tested ear is normal. |
| 26dB through 40dB | The tested ear suffers from light hearing hardness. There are no difficulties in daily conversations. However, it is expected that it is difficult to hear weak or whispering sound. Please consult an otorhinolaryngologist. |
| 41dB through 55dB | The tested ear suffers from medium hearing hardness. There are difficulties in the daily conversations. It is recommended to wear a hearing aid. |
| 56dB through 70dB | The tested ear suffers from medium-high hearing hardness. It is expected that you may have a conversation with others almost only with loud voice and you cannot hear others clearly. It is necessary to wear the hearing aid. |
| 71dB through 80dB | The tested ear suffers from high hearing hardness. Even if loud voice is heard close to your ear, you hardly hear the sound. It is required to wear the hearing aid. |

TABLE 2

High band (the method for testing the hearing ability, while looking at the screen): 4,000 Hz and 8,000 Hz

| Average threshold value | Hearing hardness grade |
| --- | --- |
| Greater than or equal to 30dB | There is a possibility of high frequency hearing loss in the high band. There are no difficulties in the daily conversations. There is a possibility that it is difficult to hear weak or whispering sound. |

TABLE 3

Low band (the method for testing the hearing ability, while looking at the screen): 250 Hz and 500 Hz

| Average threshold value | Hearing hardness grade |
| --- | --- |
| Greater than or equal to 30dB | There is a possibility of low frequency hearing loss in the low band. The low frequency hearing loss is caused by menier ds or sudden deafness. |

As mentioned above, according to the preferred embodiment of the present invention, the patient can test his hearing ability any time any place without spending time on visiting the hospital and making the reservation. Also, according to the present invention, it is not necessary to prepare the expensive equipment for the self-test. Accordingly, it is possible to save time and expenses spent on testing the hearing ability, to thus diagnose and cure the ear diseases at an early stage.

What is claimed is:

1. A method for testing hearing ability using the Internet, comprising the steps of:

a tested person selecting a method for testing the hearing ability by connecting to an internet home page;

reproducing sound having a predetermined volume of a predetermined frequency bandwidth for a set time; and calculating the hearing hardness grade of the tested person according to whether the tested person responds to the reproduced sound.

2. The method of claim 1, wherein the set time is one second.

3. The method of claim 1, wherein the sound comprises a low band of frequencies 250 Hz and 500 Hz, a conversation band of frequencies 1,000 Hz and 2,000 Hz, and a high band of frequencies 4,000 Hz and 8,000 Hz and has the volume between 0 dB and 80 dB in each frequency.

4. The method of claim 3, wherein the sounds are reproduced in the order of 1,000 Hz, 500 Hz, 1,000 Hz, and 2,000 Hz during a hearing ability test in the conversation band, the sounds are reproduced in the order of 4,000 Hz and 8,000 Hz during a hearing ability test in the high band, the sounds are reproduced in the order of 250 Hz and 500 Hz during a hearing ability test in the low band, and the sounds obtained by reducing the sound having 80 dB in units of 5 dB are reproduced to 0 dB in each frequency, in the step of reproducing the sound.

5. The method of claim 1, wherein the average threshold value of the tested person is calculated according to the response of the tested person and the hearing hardness grade of the tested person is displayed as a normal state, light hearing hardness, medium hearing hardness, medium-high hearing hardness, high hearing hardness, high frequency hearing loss, or low frequency hearing loss.

6. A method for testing hearing ability using the Internet, comprising the steps of:

(a) checking information on a tested person who connects to an Internet home page;

(b) searching and displaying the information on the tested person;

(c) selecting whether to continuously use the displayed information on the tested person;

(d) inputting and storing the information on the tested person when the information of the tested person is not searched or the searched information is determined not to be continuously used;

(e) selecting the browser of the tested person, a method for continuously testing the hearing ability, and a method for testing the hearing ability, while looking at a screen;

(f) selecting the ear whose hearing ability is to be tested when the method for continuously testing the hearing ability is selected in the step (e);

(g) reproducing the sounds having frequencies of 500 Hz, 1,000 Hz, and 2,000 Hz in a predetermined order for a set time:

(h) checking whether the reproduced sounds are heard;

(i) calculating the average threshold value of the tested person and displaying the hearing hardness grade of the tested person, according to the response of the tested person in the step (h);

(j) selecting one of a test in a low band, a test in a conversation band, and a test in a high band when the method for testing the hearing ability, while looking at the screen, is selected in the step (e);

(k) reproducing the sounds having the frequencies 250 Hz and 500 Hz, the sounds having the frequencies 500 Hz, 1,000 Hz, and 2,000 Hz, and the sounds having the frequencies 4,000 Hz and 8,000 Hz when the sounds are reproduced during the test in the low band, the test in the conversation band, and the test in the high band, respectively, for the set time;

(l) checking whether the sounds reproduced in the step (k) are heard;

(m) calculating the average threshold value of the tested person and displaying the hearing hardness grade of the tested person according to the response of the tested person in the step (l); and (n) selecting a re-test.

7. The method of claim 6, wherein the set time is one second.

8. The method of claim 7, wherein the sounds are reproduced in the order of the sounds having the frequencies 1,000 Hz, 500 Hz, 1,000 Hz, and 2,000 Hz during the continuous test and the sounds obtained by reducing the sound having 80 dB in the units of 5 dB are reproduced to 0 dB.

9. The method of claim 7, wherein the sounds are reproduced in the order of 1,000 Hz, 500 Hz, 1,000 Hz, and 2,000 Hz during the hearing ability test in the conversation band, the sounds are reproduced in the order of 4,000 Hz and 8,000 Hz during the hearing ability test in the high band, the sounds are reproduced in the order of 250 Hz and 500 Hz during the hearing ability test in the low band, and the sounds obtained by reducing the sound having 80 dB in units of 5 dB are reproduced to 0 dB in each frequency.

10. The method of claim 7, wherein the time within which it is checked whether the sounds are heard in the steps (h) and (k) is 5 seconds.

11. The method of claim 7, wherein symptoms of diseases and measures for the diseases are included in the hearing hardness grade.

12. Using a recording medium in the form of a magnetic disk, an optical disk, or a hard disk on which a method for testing hearing ability using the Internet is recorded, the method comprising the steps of:

(a) checking information on a tested person who connects to an Internet home page;

(b) searching and displaying the information on the tested person;

(c) selecting whether to continuously use the displayed information on the tested person;

(d) inputting and storing the information on the tested person when the information of the tested person is not searched or the searched information is determined not to be continuously used;

(e) selecting the browser of the tested person, a method for continuously testing the hearing ability, and a method for testing the hearing ability, while looking at a screen;

(f) selecting the ear whose hearing ability is to be tested when the method for continuously testing the hearing ability is selected in the step (e);

(g) reproducing the sounds having frequencies of 500 Hz, 1,000 Hz, and 2,000 Hz in a predetermined order for a set time;

(h) checking whether the reproduced sounds are hoard;

(i) calculating the average threshold value of the tested person and displaying the hearing hardness grade of the tested person, according to the response of the tested person in the step (h);

(j) selecting one of a test in a low band, a test in a conversation band, and a test in a high band when the method for testing the hearing ability, while looking at the screen, is selected in the step (e);

(k) reproducing the sounds having the frequencies 250 Hz and 600 Hz, the sounds having the frequencies 500 Hz, 1,000 Hz, and 2,000 Hz, and the sounds having the frequencies 4,000 Hz and 8,000 Hz when the sounds are reproduced during the test in the low band, the test in the conversation band, and the test in the high band. respectively, for the set time:

(l) checking whether the sounds reproduced in the step (k) are heard;

(m) calculating the average threshold value of the tested person according to the response of the tested person in the step (l) and displaying the hearing hardness grade of the tested person and symptoms of diseases and measurements for the diseases according to the hearing hardness grade; and (n) selecting a re-test.

* * * * *